United States Patent [19]

Aneja

[11] Patent Number: 4,492,807
[45] Date of Patent: Jan. 8, 1985

[54] METHOD FOR PURIFICATION OF BISPHENOL A

[75] Inventor: Viney P. Aneja, Schenectady, N.Y.

[73] Assignee: General Electric Company, Schenectady, N.Y.

[21] Appl. No.: 487,546

[22] Filed: Apr. 22, 1983

[51] Int. Cl.³ .............................................. C07C 37/70
[52] U.S. Cl. .................................... 568/724; 568/730
[58] Field of Search ............................. 568/724, 730

[56] References Cited

U.S. PATENT DOCUMENTS

| | | | |
|---|---|---|---|
| 3,192,270 | 6/1965 | Meyer et al. | 568/724 |
| 3,919,330 | 11/1975 | Kwantes et al. | 568/724 |
| 3,972,950 | 8/1976 | Kwantes | 568/724 |
| 4,192,955 | 3/1980 | Renitz | 568/724 |
| 4,209,646 | 6/1980 | Gac et al. | 568/724 |
| 4,294,993 | 10/1981 | Li | 568/724 |
| 4,300,000 | 11/1981 | Reinitz | 568/724 |
| 4,320,234 | 3/1982 | Mark | 568/724 |
| 4,414,422 | 11/1983 | Ash et al. | 568/724 |

Primary Examiner—Werren B. Lone
Attorney, Agent, or Firm—William H. Pittman; James C. Davis, Jr.; James Magee, Jr.

[57] ABSTRACT

Bisphenol A is commonly purified by a method which includes formation of an adduct thereof with phenol from a liquid mixture to which water has been added. This method is improved by the simultaneous addition of an organic liquid in an amount up to about 15% by weight of the mixture. The preferred organic liquids are acetone and toluene.

12 Claims, 1 Drawing Figure

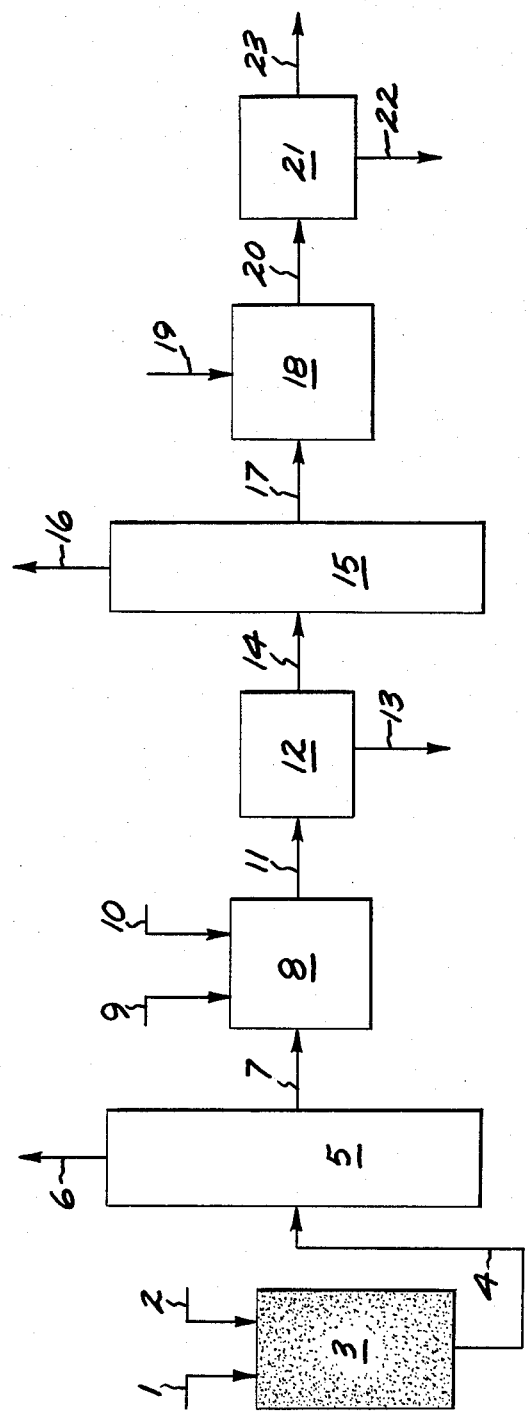

METHOD FOR PURIFICATION OF BISPHENOL A

This invention relates to the preparation and purification of bisphenol A, and more particularly to improvements in a method for the purification and isolation thereof.

Bisphenol A, or 2,2-bis(4-hydroxyphenyl)propane, is a valuable chemical intermediate for the production of various resinous materials, notably epoxy resins and polycarbonates. It is conveniently produced by the acid-catalyzed condensation of phenol and acetone. The reaction mixture obtained by the condensation may contain, in addition to bisphenol A, excess phenol, unreacted acetone, water of reaction and various by-products including 2-(2-hydroxyphenyl)-2-(4-hydroxyphenyl)-propane (hereinafter "o,p-bisphenol") and higher condensation products. Separation of the bisphenol A from this mixture in relatively pure form is, of course, necessary.

Many purification procedures for bisphenol A involve the formation of an equimolar adduct thereof with phenol (hereinafter "adduct"). Illustrative procedures of this type are disclosed in U.S. Pat. Nos. 3,192,270 and 4,209,646. According to those procedures, a mixture of impure bisphenol A, phenol and water is liquefied by heating and is then cooled (sometimes after removal of an aqueous phase) to form the adduct, which is frequently separated by crystallization and from which phenol is subsequently removed to yield bisphenol A of relatively high purity. The formation of the adduct permits purification at lower temperatures and with less energy input then other purification methods.

The addition of water as disclosed in the aforementioned patents results in a considerable improvement in the yield of bisphenol A recovered. However, the purity of the product is often still so low that further expensive and burdensome purification steps are necessary. Another disadvantage frequently encountered is that the adduct is contaminated with extraneous material, chiefly phenol, if the temperature to which the mixture is cooled is less than about 50° C., but the use of higher temperatures results in the loss of a large amount of bisphenol A by dissolution in excess phenol. In addition, the efficiency of the purification process may be impaired by the deposition of adduct and excess phenol as scale on various parts of the apparatus.

A principal object of the present invention, therefore, is to provide a method for the production of bisphenol A which affords a substantially pure product with a minimum of purification steps.

A further object is to purify bisphenol A by a method substantially free of scaling and other undesirable phenomena.

A still further object is to provide a purification method which is adaptable to either batch or continuous production of bisphenol A.

Other objects will in part be obvious and will in part appear hereinafter.

The present invention is an improvement in a method for purifying bisphenol A which includes the steps of adding up to about 15% by weight of water to a mixture comprising impure bisphenol A and phenol, heating said mixture to a temperature no higher than 100° C. at which it is entirely liquid, and cooling said mixture to form an adduct of bisphenol A and phenol. The improvement comprises also adding to said mixture up to about 15%, by weight of said mixture, of a substantially inert organic liquid.

The method of this invention is applicable to any bisphenol A production method which includes the above-described steps. Typically, a phenol-acetone reaction is carried out by blending acetone with a large excess of phenol and contacting the blend with an acidic catalyst, which may be a mineral acid such as sulfuric or hydrochloric acid or a cation exchange resin in the acid form. Following the condensation reaction, the mixture may be neutralized if necessary and stripped to remove volatile materials such as unreacted acetone, water of reaction and some phenol. The non-volatile materials are passed to an adduct formation stage in which water is added and the mixture is heated until it is entirely liquid, typically within the range of about 80°–100° C. and preferably about 85°–95° C.

According to the present invention, an organic liquid is added simultaneously with the water. The only requirement for such liquid is that it be substantially inert under the conditions of use; that is, that it not react with bisphenol A or phenol in the presence of water under substantially neutral conditions. It is also strongly preferred that the liquid dissolve a substantial proportion of the impurities or by-products produced in the phenol-acetone reaction.

As will be apparent from the foregoing, a wide variety of organic liquids, both polar and substantially non-polar, may be used. Among the useful polar liquids are ketones such as acetone and methyl ethyl ketone; alkanols such as the butanols, pentanols, hexanols, octanols and decanols; and esters such as the butyl acetates, pentyl propionates, hexyl acetates and heptyl acetates. Illustrative substantially non-polar liquids are aliphatic hydrocarbons such as the pentanes, hexanes, octanes and nonanes; chlorinated aliphatic hydrocarbons such as methylene chloride, chloroform and 1,2-dichloroethane; aromatic hydrocarbons such as benzene, toluene, the xylenes and ethylbenzene; and substituted aromatic hydrocarbons such as chlorobenzene, o-dichlorobenzene, nitrobenzene and m-nitrotoluene. Mixtures of these liquids may also be used.

The preferred polar and substantially non-polar organic liquids, respectively, are the ketones and aromatic hydrocarbons. Acetone and toluene are especially preferred because of their availability and relatively low cost. The latter is most preferred because it forms an azeotrope with water and facilitates its removal; the former is also of considerable usefulness because it is a reactant in the synthesis process rather than an extraneous material.

The mole ratio of phenol to bisphenol A in the mixture from which the adduct is crystallized is usually at least about 4:1 and preferably at least about 5:1. There is no upper limit of this mole ratio, but a higher value than about 9:1 seldom has any purpose.

The amounts of water and organic liquid added to the adduct are, as previously mentioned, up to about 15% of the total weight of the mixture. The preferred range of each is about 2–5%.

Following addition of water and the organic liquid, the mixture is cooled to a temperature at which the adduct forms. At this stage it is usually preferred to crystallize and separate the adduct. However, adduct formation without crystallization has certain advantages, chiefly relating to the thermodynamics of the process. Therefore, the invention is not limited to situations where adduct crystallization and separation occurs.

The adduct formation (and usually crystallization) temperature is below about 60° C., typically within the range of about 0°–35° C. and preferably about 10°–30° C. An advantage of the present invention is that the mixture may be cooled to a substantially lower temperature than ordinarily permitted using previously known procedures, enabling the recovery of a higher proportion of adduct without sacrificing purity.

Cooling may be effected at atmospheric pressure or at reduced pressure. The latter typically corresponds to the vapor pressure of the system, as disclosed in the aforementioned U.S. Pat. No. 4,209,646. In addition to decreasing the energy requirements of the process, the use of reduced pressure may eliminate the need for agitation or enable more gentle agitation, thus promoting formation of large crystals.

After the adduct has crystallized, most of the impurities are in the liquid phase and may be easily separated from the adduct by filtration, centrifugation or the like. It is frequently preferred to maximize impurity removal by washing the separated adduct with liquid phenol. The adduct may then be broken by known methods such as extraction, distillation, steam stripping or prilling, yielding high purity bisphenol A. If further purification thereof is necessary, it may be effected by a further identical adduct crystallization step, by crystallization from water or a suitable solvent, or by other methods known in the art.

Reference is now made to the drawing which is a schematic diagram of a typical system for the preparation of bisphenol A in which the method of this invention is utilized. It should be understood that the system shown in the drawing is merely illustrative and that the method of this invention may be used in any bisphenol A production system which includes an adduct crystallization step. Heating, agitation, recycling and the like where necessary are effected by conventional means known to those skilled in the art.

In the drawing, phenol and acetone are introduced at 1 and 2 respectively into reaction stage 3, comprising one or more reactor vessels charged with a cation exchange resin in the acid form and maintained at a temperature of about 70° C. The molar ratio of phenol to acetone is typically about 8:1. The effluent from reactor 3, which comprises bisphenol A, unreacted acetone and phenol, water of reaction and impurities including o,p-bisphenol, passes via line 4 into stripping stage 5, typically a column from which water of reaction, acetone and some phenol are removed by distillation through overhead line 6. If desired, the acetone and phenol may be separated and recycled.

The stripped mixture, comprising bisphenol A, remaining phenol and impurities, passes via line 7 into adduct crystallization stage 8, where it is maintained at about 85°–95° C. during the addition of water and organic liquid through lines 9 and 10, respectively. It is then cooled to about 55° C., at which temperature the adduct crystallizes. The mixture then passes through line 11 to centrifugation stage 12, typically a basket centrifuge, from which mother liquor comprising excess phenol, a minor amount of bisphenol A, water, organic liquid and impurities are removed through line 13.

The disposition of the mother liquor from centrifugation stage 12 will depend to some extent on the identity of the organic liquid used. If it is toluene or some other liquid which forms an azeotrope with water, it may be removed by azeotropic distillation and recycled through line 10. If it is acetone, it may be combined with the material discharged from stripping stage 5 via line 6. Other organic liquids may be recovered by suitable means known in the art. Water may be recycled via line 9 to adduct crystallization stage 8, and other constituents may be recycled to reaction stage 3. Any o,p-bisphenol in the material recycled to the reaction stage may be isomerized to bisphenol A upon contact with the ion exchange resin.

The crystalline material separated in centrifugation stage 12 comprises principally adduct, but may also contain a very minor proportion of impurities. It is removed via line 14 and passes to stripping stage 15, typically a thin film stripper of the Luwa type. The stripped material which is removed overhead via line 16 comprises predominantly phenol, with a very small proportion of bisphenol A, and may be recycled if desired. The non-volatile material removed through line 17 consists of purified bisphenol A with very small proportions of residual phenol and impurities.

When further purification is desired, the bisphenol A from line 17 is fed to a crystallization stage 18 into which water is introduced through line 19. The temperature during water introduction is ordinarily about 95° C., and the mixture is then cooled to about 55° C. whereupon the bisphenol A crystallizes. The mixture passes through line 20 into centrifugation stage 21 (similar to 12), from which mother liquor comprising water, remaining phenol, a very small proportion of bisphenol A and remaining impurities is withdrawn through line 22 and may be recycled. The solid product withdrawn through line 23 is essentially pure bisphenol A.

The method of this invention is useful in both batch and continuous processes for the purification of bisphenol A. However, its use is particularly advantageous when adduct separation is a continuous process since the purity of the product is frequently higher than that obtained in batch processes.

The invention is illustrated by the following Examples 1–7. Examples 1–6 illustrate batch processes, and Example 7 the preferred continuous process. Example 5 illustrates a procedure wherein the temperature to which the mixture is cooled to crystallize the adduct is above 50° C., and Examples 1–4, 6 and 7 illustrate the preferred embodiment in which said temperature is within the range of 10°–30° C.

In the examples, crude bisphenol A was mixed with phenol, organic liquid and water and the mixture was heated under nitrogen, with stirring, to a temperature at which it was entirely liquid. It was then cooled under nitrogen, with stirring, and the adduct crystals were separated in a basket centrifuge. In Examples 4 and 5, the crystals were washed with liquid phenol. In Example 7, adduct separation was effected by feeding the liquid mixture at 150 ml. per minute to a continuous crystallizer and then to the centrifuge.

The relevant parameters and results of Examples 1–7 are given in the following table. All percentages are by weight; percentages of water and organic liquid are based on total weight of crude bisphenol A and phenol. "Heating temperature" and "cooling temperature", are, respectively, the highest temperature to which the liquid mixture is heated and the lowest temperature to which it is cooled prior to adduct removal. In Example 7, the steady-state cooling temperature is given. "Recovery" is the amount of adduct recovered expressed as a percentage of the theoretical amount based on bisphenol A. "Purity ratio" is the weight ratio of bisphenol A to the indicated by-products and impurities. As a general rule, a value of less than about 200 for either purity ratio indicates that further purification is required before use. It is, of course, preferred for both purity ratios to be as high as possible.

|  | EXAMPLE | | | | | | |
| --- | --- | --- | --- | --- | --- | --- | --- |
|  | 1 | 2 | 3 | 4 | 5 | 6 | 7 |
| Mole ratio, phenol:bisphenol A | 5.4 | 8.5 | 8.5 | 5.15 | 4.5 | 5.02 | 5.04 |
| Water amount, % | 3.9 | 2.7 | 4.4 | 4.0 | 4.0 | 4.2 | 3.9 |
| Organic liquid: | | | | | | | |
| Identity | Acetone | Acetone | Acetone | Toluene | Toluene | Toluene | Toluene |
| Amount, % | 3.9 | 2.7 | 4.4 | 4.2 | 4.0 | 4.1 | 3.8 |
| Heating temperature, °C. | 85 | 85 | 85 | 95 | 95 | 85 | 86 |
| Cooling temperature, °C. | 12 | 28 | 12 | 13 | 55 | 25 | 25 |
| Recovery, % | 88 | 74 | 77 | 90 | 35 | 80 | 80 |
| Purity ratio: | | | | | | | |
| Based on o,p-bisphenol | 387 | 711 | 599 | 1380 | 1320 | 384 | 495 |
| Based on other impurities | 454 | 1185 | 2490 | 1872 | 1268 | 667 | 954 |

Several things are apparent from the table. In the first place, a comparison of Examples 4 and 5 shows that the use of a cooling temperature within the preferred range of 10°-30° C., permitted by the present invention in contrast to many prior art processes, results in a pronounced increase in recovery without a material sacrifice in product purity. (It is not believed that recovery is materially affected by the presence or absence of organic liquid in a process of the type represented in Example 5.) In the second place, the improvement in a phenol wash is apparent from a comparison of Examples 4-5 with Examples 6-7. In the third place, a comparison of Example 1 with Examples 2-3 shows that an increase in the proportion of phenol in the feed increases purity with some sacrifice of recovery. Finally, the improvement in purity with no accompanying sacrifice of recovery which results from continuous operation of the process is shown by a comparison of Examples 6 and 7.

What is claimed is:

1. In a method for purifying bisphenol A which includes the steps of adding up to about 15% by weight of water to a mixture comprising impure bisphenol A and phenol, heating said mixture to a temperature no higher than 100° C. at which it is entirely liquid, and cooling said mixture to form an adduct of bisphenol A and phenol, the improvement which comprises adding to said mixture simultaneously with said water, up to about 15% by weight of an organic liquid which will not react with bisphenol A or phenol in the presence of water under substantially neutral conditions and which dissolves a substantial proportion of the impurities or by-products produced in the reaction forming said bisphenol A, and subsequently crystallizing and separating said adduct.

2. A method according to claim 1 wherein the organic liquid is at least one of acetone and toluene.

3. A method according to claim 2 wherein the mole ratio of phenol to bisphenol A in the mixture is at least about 4:1.

4. A method according to claim 3 wherein about 2-5% each of water and the organic liquid are added.

5. A method according to claim 4 wherein the mixture is heated to a temperature within the range of about 85°-95° C.

6. A method according to claim 5 wherein the mixture is cooled to a temperature below about 60° C.

7. A method according to claim 6 wherein the mixture is cooled to a temperature within the range of about 10°-30° C.

8. A method according to claim 7 wherein the adduct is washed with liquid phenol after separation.

9. A method according to claim 8 wherein the organic liquid is toluene.

10. A method according to claim 8 wherein the organic liquid is acetone.

11. A method according to claim 1, 3, 5, 7, 9 or 10 wherein adduct separation is a continuous process.

12. A method for purifying bisphenol A which comprises mixing impure bisphenol A, phenol and about 2-5% by weight each of water and toluene, based on said bisphenol A and phenol; heating the resulting mixture to a temperature within the range of about 85°-95° C. at which it is entirely liquid; cooling said mixture to a temperature within the range of about 10°-30° C. to separate the crystalline adduct of bisphenol A and phenol; continuously separating said crystalline adduct; washing the adduct crystals with liquid phenol; and removing the phenol from said adduct to yield high purity bisphenol A.

* * * * *